United States Patent [19]

Perchonock

[11] 4,093,807

[45] June 6, 1978

[54] TRICYCLIC β-LACTAMS

[75] Inventor: Carl David Perchonock, Philadelphia, Pa.

[73] Assignee: SmithKline Corporation, Philadelphia, Pa.

[21] Appl. No.: 810,127

[22] Filed: Jun. 27, 1977

[51] Int. Cl.² ............................................ C07D 251/72
[52] U.S. Cl. .................................... 544/183; 424/249
[58] Field of Search ......................................... 544/183

[56] References Cited
PUBLICATIONS

Hashimoto et al., J. Amer. Chem. Soc., vol. 98, pp. 3023–3025 (1976).
Bryan et al., J. Amer. Chem. Soc., vol. 99, pp. 2353–2355 (1977).
Finestone et al., J. Med. Chem., vol. 20, pp. 551–556.
Derwent Belgian Patent Reports, 827,926.

*Primary Examiner*—John M. Ford
*Attorney, Agent, or Firm*—Stuart R. Suter; Alan D. Lourie; William H. Edgerton

[57] ABSTRACT

A new β-lactam system containing a tricyclic ring nucleus is disclosed. In addition to the β-lactam, the new nucleus contains a cyclic hydrazide moiety. The compounds have antibacterial activity.

11 Claims, No Drawings

TRICYCLIC β-LACTAMS

BACKGROUND

Work on β-lactam antibiotics has centered mainly on penicillins and cephalosporin compounds, both of which have bicyclic ring systems. Recently, new β-lactam systems which maintain their antibiotic properties have been reported. Examples include nocardicin [*J. Amer. Chem. Soc.*, 98, 3023 (1976)], which contains a monocyclic β-lactam nucleus, clavulanic acid (Belgian Pat. No. 827,926), which has an oxygen-containing bicyclic β-lactam nucleus, and bicyclic systems related to cephalosporins in which the sulfur atom has been moved to another position, [*J. Amer. Chem. Soc.*, 99, 2353 (1977)] and has been replaced by oxygen or a methylene group [*J. Med. Chem.*, 20, 551 (1977)]. These systems are not believed material prior art to the present invention.

I have now prepared a novel tricyclic β-lactam system which contains additional nitrogen atoms; in particular, the 8,11-dioxo-1,3,7-triazatricyclo[7.2.0.0$^{3,7}$]undecane and the 9,12-dioxo-1,3,8-triazatricyclo[8.2.0.0$^{3,8}$]dodecane nuclei.

DESCRIPTION OF THE INVENTION

The compounds of this invention are defined by the following chemical formula

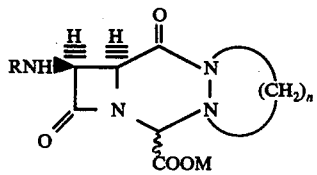

wherein
R is phenoxyacetyl or 2-thienylacetyl,
n is 3 or 4, and
M is hydrogen, a carboxylic acid protective ester residue, or a pharmaceutically acceptable non-toxic cation.

The term "a carboxylic acid protective ester group" is one which has a clear and definite meaning within the art. Many ester groups are known and used in the art to protect a carboxylic acid group from interfering with chemical reactions or from being reacted on themselves in undesired ways. Many examples of such ester groups are set forth in the chemical literature, including review articles and books such as "Protective Groups in Organic Chemistry", McOmie ed., Plenum Press, New York, 1973. Examples of the most common esters included benzyl, benzhydryl, and trichloroethyl. The selection of which ester group to use depends on various factors including subsequent reaction conditions and desired methods of removal. The selection of the proper ester group is within the ability of persons skilled in the art.

Pharmaceutically acceptable non-toxic cations are also well-known in the art. In general, they include alkali metal cations, alkaline earth cations and organic or inorganic ammonium cations. The sodium and potassium salts are particularly advantageous. Again the selection of useful and proper cations is within the ability of persons skilled in the art.

The compounds of this invention are prepared by a totally synthetic route with the appropriate acylamino monocyclic β-lactam (1) as starting material. Compound 1 is prepared from compound 2 by methods disclosed in Belgian Pat. No. 841,234.

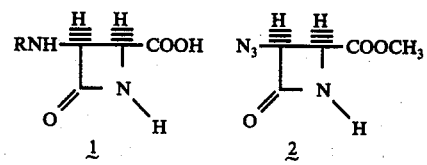

Scheme I outlines the reaction sequence to convert compound 1 into the compounds of this invention. The carboxylic acid 1 is condensed with pyrazolidine (n=3) or hexahydropyridazine (n=4) with the aid of a coupling reagent such as dicyclohexylcarbodiimide (DCC) to give compound 3. Cyclization of compound 3 into the desired compounds of this invention is effected by treatment with an ester of glyoxylic acid in the presence of an acid catalyst such as boron trifluoride etherate. Cleavage of the ester group gives the novel antibacterially active compounds.

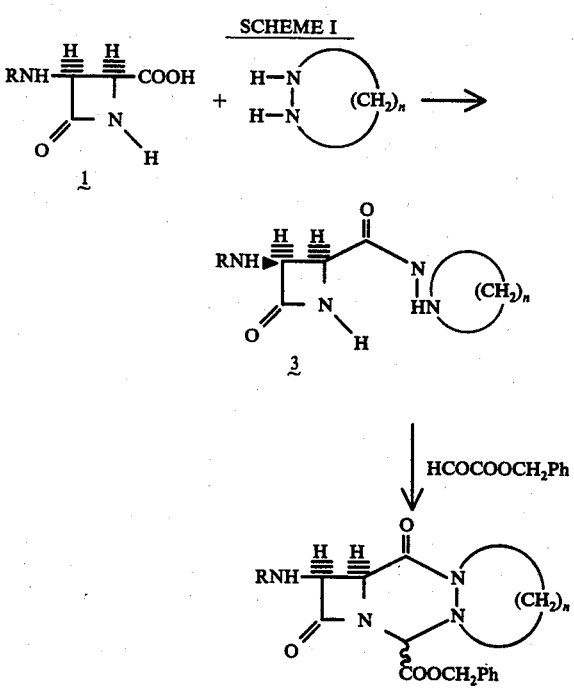

The carboxyl group at position 2 may be in the α or β configuration. Both configurations as well as mixtures of the two are within the scope of this invention.

The compounds of this invention where M is hydrogen or a cation have antibacterial activity against Gram-positive bacteria, especially *Staphococcus aureus* and *B. subtilis*. They are useful for sterilization of laboratory glassware or for treating bacterial infections in animals. Minimum inhibitory concentrations (MIC) ranged from 25 to >200 μg/ml against species of *Staph. aureus* when tested by the standard agar inclusion methods.

The compounds of this invention where M is a protective ester group are useful as intermediates for the antibacterially active compounds.

The following examples are presented to illustrate general methods of preparing the compounds of this invention to one skilled in the art and are not to be construed as limiting the scope thereof. All temperatures are given in degrees Centigrade.

EXAMPLE 1

11-β-Phenoxyacetamido-9,12-dioxo-1,3,8-triazatricyclo[8.2.0.0$^{3,8}$]-dodecane-2-carboxylic acid To a solution of cis-3-phenoxyacetamido-4-oxoazetidine-2-carboxylic acid (1.97 g, 7.47 mmol) and dicyclohexylcarbodiimide (1.7 g, 8.22 mmol) in freshly distilled tetrahydrofuran (75 ml) was added a solution of hexahydropyridazine (0.74 g, 8.59 mmol) in tetrahydrofuran (3 ml). The reaction was stirred under a nitrogen atmosphere overnight. The solution was filtered and the solid washed with ether. The solid was suspended in warm 2% methanol in chloroform (40 ml), filtered and the procedure repeated. The resulting solid was chromatographed on silica gel (40 g) and eluted with a 2% to 5% gradient of methanol in chloroform to give the hydrazide product (0.94 g). The reaction filtrate was evaporated and the residue chromatographed as outlined above to give additional product. Recrystallization of the product from chloroform-ether gave a total yield of 1.13 g (46%), mp 185°–187°.

The above hydrazide (0.945 g, 2.84 mmol) was added to a solution of benzyl glyoxalate (0.65 g, 3.98 mmol) in freshly distilled tetrahydrofuran (60 ml). To the resulting solution was added boron trifluoride etherate (0.47 ml, 3.86 mmol) dropwise and the reaction stirred overnight under a nitrogen atmosphere. The solution was diluted with ethyl acetate (250 ml) and washed with saturated brine and then 5% NaHCO$_3$. The dried solution was evaporated to an oil, which was triturated with ether. The oil was dissolved in 7:3 benzene-ethyl acetate and cooled at 0° for two days to precipitate a solid (382 mg). The solid was collected and the filtrate was chromatographed on silica gel (40 g) and eluted with 7:3 benzene-ethyl acetate to give additional product (50 mg). The solids were combined and recrystallized from ethyl acetate to give pure product (0.29 g, 22%), mp 166°–167° (epimer 1). The chromatography also afforded 142 mg (10%) of epimer 2, mp 146°–147.5°.

To a solution of each epimeric benzyl ester (100 mg, 0.21 mmol) in dioxane (10 ml) was added a solution of NaHCO$_3$ (18.4 mg, 0.22 mmol) in water. The resulting solution was hydrogenated for 1 hour at atmospheric pressure in the presence of 10% Pd on carbon. The solution was filtered and lyophilized to give the two epimers of the title compound as their sodium salt, 83 mg (97%) of each.

EXAMPLE 2

10-β-Phenoxyacetamido-8,11-dioxo-1,3,7-triazatricyclo[7.2.0.0$^{3,7}$]-undecane-2-carboxylic acid Dicyclohexylcarbodiimide (0.422 g, 2.05 mmol) and cis-3-phenoxyacetamido-4-oxoazetidine-2-carboxylic acid (0.522 g, 1.97 mmol) were dissolved in distilled tetrahydrofuran (20 ml) and pyrazolidine (0.146 g, 2.02 mmol) in tetrahydrofuran (5 ml) was added to this. The reaction was stirred under nitrogen overnight and then the solid precipitate was removed by filtration. The filtrate was evaporated and the resulting residue was recrystallized from tetrahydrofuran-isopropyl ether to give the hydrazide as a white solid, mp 173°–175°.

To a solution of the above hydrazide (ca. 1.17 mmol) and freshly distilled benzyl glyoxalate (0.253 g, 1.54 mmol) in freshly distilled tetrahydrofuran (16 ml) was added boron trifluoride etherate (0.219 g, 1.54 mmol). The solution was stirred 1.5 hours and then diluted with ethyl acetate (75 ml). The resulting solution was washed with brine and 5% NaHCO$_3$. The dried solution was evaporated and the residue was chromatographed on silica gel (50 g) with 1:1 ethyl acetate-chloroform as eluant to give the benzyl ester of the title product; 66 mg, mp 174°–176°.

To a solution of the benzyl ester (47 mg, 0.1 mmol) in dioxane (4 ml) was added a solution of NaHCO$_3$ (10 mg) in water (2 ml) and the resulting solution was hydrogenated at atmospheric pressure for 30 minutes in the presence of 10% Pd on carbon. The reaction mixture was filtered and lyophilized to give the title compound as its sodium salt, 38 mg.

EXAMPLE 3

10-β-(2-Thienylacetamido)-8,11-dioxo-1,3,7-triazatricyclo[7.2.0.0$^{3,7}$]undecane-2-carboxylic acid To a solution of 3-(2-thienylacetamido)-4-oxoazetidine-2-carboxylic acid (500 mg, 1.97 mmol) and N-hydroxysuccinimide (238 mg, 2.06 mmol) in tetrahydrofuran (20 ml) was added dropwise a solution of dicyclohexylcarbodiimide (416 mg, 2.02 mmol) in tetrahydrofuran (5 ml). The reaction was stirred 1 hour and then filtered. The filtrate was treated with pyrazolidine (154 mg, 2.14 mmol) in tetrahydrofuran (1 ml). The solution was stirred under a nitrogen atmosphere overnight, decanted from a gummy residue, and evaporated. The foam residue was dissolved in ethyl acetate (50 ml) and 5% NaHCO$_3$ (25 ml). The phases were separated and the organic phase was washed with another portion of NaHCO$_3$. The combined aqueous layers were repeatedly extracted with ethyl acetate and the combined ethyl acetate layers were dried and evaporated to give solid hydrazide (413 mg).

To a slurry of the above product (413 mg) in tetrahydrofuran (20 ml) was added a solution of freshly distilled benzyl glyoxalate (0.22 g, 1.34 mmol) in tetrahydrofuran (1 ml). After stirring 10 minutes, boron trifluoride etherate (0.12 ml, 185 mg, 1.3 mmol) was added. The reaction was stirred under nitrogen for one hour and then poured into ethyl acetate (100 ml). The solution was washed with 5% NaHCO$_3$ and brine, dried and evaporated to an oil which was chromatographed on silica gel (40 g). Elution with 1:2 chloroform:ethyl acetate gave the benzyl ester of the title compound (260 mg).

The benzyl ester (42 mg) was hydrogenated in dioxane (8 ml) and water (2 ml) in the presence of NaHCO$_3$ (9 mg) and 10% Pd on carbon (45 mg) at atmospheric pressure for 60 minutes. Additional catalyst (48 mg) was added, followed 30 minutes later with more catalyst (50 mg). After another 40 minutes, the catalyst was removed and the solution was diluted with water (2 ml) and extracted with ethyl acetate. The aqueous solution was lyophilized to give the title product, 28 mg.

EXAMPLE 4

11-β-(2-Thienylacetamido)-9,12-dioxo-1,3,8-triazatricyclo[8.2.0.0$^{3,8}$]dodecane-2-carboxylic acid Substitution of hexahydropyridazine for pyrazolidine in Example 3 gives the corresponding hydrazide. The hydrazide is reacted further with benzyl glyoxalate and then hydrogenated, all according to the procedure of Example 3, to give the title product.

I claim:
1. A compound of the formula

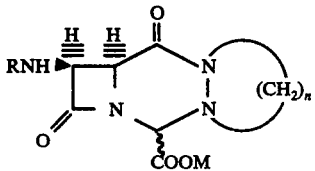

where

R is phenoxyacetyl or 2-thienylacetyl, n is 3 or 4, 1 and

M is hydrogen, a pharmaceutically acceptable non-toxic cation, or a carboxylic acid protective ester residue.

2. A compound as claimed in claim 1 where $n$ is 3.

3. A compound as claimed in claim 2 being 10-β-phenoxyacetamido-8,11-dioxo-1,3,7-triazatricyclo[7.2.0.0$^{3,7}$]-undecane-2-carboxylic acid.

4. The compound of claim 3 as its sodium or potassium salt.

5. The compound of claim 3 as its benzyl ester.

6. A compound as claimed in claim 2 being 10-β-(2-thienylacetamido)-8,11-dioxo-1,3,7-triazatricyclo-[7.2.0.0$^{3,7}$]undecane-2-carboxylic acid.

7. The compound of claim 6 as its sodium or potassium salt.

8. The compound of claim 6 as its benzyl ester.

9. A compound as claimed in claim 1 where $n$ is 4.

10. A compound as claimed in claim 9 being 11-β-phenoxyacetamido-9,12-dioxo-1,3,8-triazatricyclo[8.2.0.0$^{3,8}$]-dodecane-2-carboxylic acid.

11. A compound as claimed in claim 9 being 11-β-(2-thienylacetamido)-9,12-dioxo-1,3,8-triazatricyclo-[8.2.0.0$^{3,8}$]dodecane-2-carboxylic acid.

UNITED STATES PATENT AND TRADEMARK OFFICE
CERTIFICATE OF CORRECTION

PATENT NO. : 4,093,807
DATED : June 6, 1978
INVENTOR(S) : Carl David Perchonock

It is certified that error appears in the above-identified patent and that said Letters Patent are hereby corrected as shown below:

Column 5, line 14, "n is 3 or 4, 1 and" should read "n is 3 or 4, and"

Signed and Sealed this

Thirty-first Day of October 1978

[SEAL]

Attest:

RUTH C. MASON
Attesting Officer

DONALD W. BANNER
Commissioner of Patents and Trademarks